(12) United States Patent
Pintat et al.

(10) Patent No.: US 9,388,136 B2
(45) Date of Patent: Jul. 12, 2016

(54) TERT-BUTYL N-[2-{4-[6-AMINO-5-(2,4-DIFLUOROBENZOYL)-2-OXOPYRIDIN-1(2H)-YL]-3,5-DIFLUOROPHENYL}ETHYL]-L-ALANINATE OR A SALT, HYDRATE OR SOLVATE THEREOF

(71) Applicant: Chroma Therapeutics Ltd., Abingdon, Oxfordshire (GB)

(72) Inventors: Stéphane Pintat, Abingdon (GB); Stephen John Davies, Abingdon (GB); David Festus Charles Moffat, Abingdon (GB)

(73) Assignee: Chroma Therapeutics Ltd, Abingdon, Oxfordshire (GB)

( * ) Notice: Subject to any disclaimer, the term of this patent is extended or adjusted under 35 U.S.C. 154(b) by 0 days.

(21) Appl. No.: 14/436,404

(22) PCT Filed: Oct. 15, 2013

(86) PCT No.: PCT/GB2013/052689
§ 371 (c)(1),
(2) Date: Apr. 16, 2015

(87) PCT Pub. No.: WO2014/060742
PCT Pub. Date: Apr. 24, 2014

(65) Prior Publication Data
US 2015/0246883 A1  Sep. 3, 2015

(30) Foreign Application Priority Data

Oct. 17, 2012  (GB) .................................... 1218640.9
Apr. 16, 2013  (GB) .................................... 1306881.2

(51) Int. Cl.
*C07D 213/73* (2006.01)
*A61K 31/4412* (2006.01)

(52) U.S. Cl.
CPC .................................... *C07D 213/73* (2013.01)

(58) Field of Classification Search
None
See application file for complete search history.

(56) References Cited

U.S. PATENT DOCUMENTS

| | | |
|---|---|---|
| 7,932,246 B2 | 4/2011 | Moffat et al. |
| 7,939,666 B2 | 5/2011 | Davidson et al. |
| 7,973,181 B2 | 7/2011 | Davidson et al. |
| 8,003,695 B2 | 8/2011 | Moffat et al. |
| 8,044,211 B2 | 10/2011 | Moffat et al. |
| 8,106,091 B2 | 1/2012 | Moffat et al. |
| 8,148,531 B2 | 4/2012 | Davidson et al. |
| 8,211,900 B2 | 7/2012 | Davidson |
| 8,637,547 B2 | 1/2014 | Davidson et al. |
| 8,686,032 B2 | 4/2014 | Davidson et al. |
| 8,778,953 B2 | 7/2014 | Moffat et al. |
| 2009/0203711 A1 | 8/2009 | Moffat |
| 2009/0215800 A1 | 8/2009 | Davidson et al. |
| 2010/0004250 A1 | 1/2010 | Philips et al. |
| 2010/0010057 A1 | 1/2010 | Moffat et al. |
| 2010/0216802 A1 | 8/2010 | Moffat et al. |
| 2010/0267774 A1 | 10/2010 | Moffat et al. |
| 2010/0317678 A1 | 12/2010 | Moffat et al. |
| 2010/0317865 A1 | 12/2010 | Davidson et al. |
| 2011/0039920 A1 | 2/2011 | Moffat et al. |
| 2011/0046210 A1 | 2/2011 | Moffat et al. |
| 2011/0190306 A1 | 8/2011 | Moffat et al. |
| 2012/0035251 A1 | 2/2012 | Drummond et al. |
| 2012/0149736 A1 | 6/2012 | Donald et al. |
| 2013/0143926 A1 | 6/2013 | Donald et al. |
| 2013/0197042 A1 | 8/2013 | Davidson et al. |
| 2013/0303576 A1 | 11/2013 | Donald et al. |
| 2014/0010762 A1 | 1/2014 | Charlton et al. |
| 2014/0088159 A1 | 3/2014 | Drummond et al. |
| 2014/0155439 A1 | 6/2014 | Donald et al. |
| 2014/0163042 A1 | 6/2014 | Davidson et al. |
| 2015/0126534 A1 | 5/2015 | Davidson et al. |

FOREIGN PATENT DOCUMENTS

| | | |
|---|---|---|
| EP | 0505321 A2 | 9/1992 |
| WO | WO-03076405 A1 | 9/2003 |
| WO | WO-2007129040 A1 | 11/2007 |
| WO | WO-2009060160 A1 | 5/2009 |
| WO | WO-2014001802 A1 | 1/2014 |

OTHER PUBLICATIONS

Barone et al, "SB 239063, a Second-Generation p38 Mitogen-Activated Protein Kinase Inhibitor, Reduces Brain Injury and Neurological Deficits in Cerebral Focal Ischemia", J. Pharmacol. Exp. Ther., No. 296, 2001, pp. 312-321.

Behr et al, "Hypertensive End-Organ Damage and Premature Mortality Are P38 Mitogen-Activated Protein Kinase-Dependent in a Rat Model of Cardiac Hypertrophy and Dysfunction", Circulation, No. 104, 2001, pp. 1292-1298.

Borsch et al, "The Cyanohydridoborate Anion as a Selective Reducing Agent", J. Am. Chem. Soc., No. 93(23), 1971, pp. 2897-2904.

(Continued)

*Primary Examiner* — Zinna Northington Davis
(74) *Attorney, Agent, or Firm* — Norton Rose Fulbright US LLP

(57) ABSTRACT

The present invention provides a compound which is: tert-butyl N-[2-{4-[6-amino-5-(2,4-difluorobenzoyl)-2-oxopyridin-1(2H)-yl]-3,5-difluorophenyl}ethyl)-L-alaninate or a salt, hydrate or solvate thereof. The present invention also provides a pharmaceutical composition comprising the compound together with one or more pharmaceutically acceptable carriers and/or excipients. The compound and composition are useful for inhibiting the activity of a p38 MAP kinase enzyme. As such they may be used in the treatment of a autoimmune or inflammatory disease, or a cell proliferative disease. In addition, the invention provides an acid produced by hydrolysis of the ester group of the compound of the invention. The acid is N-[2-{4-[6-amino-5-(2,4-difluorobenzoyl)-2-oxopyridin-1(2H)-yl]-3,5-difluorophenyl}ethyl)-L-alanine.

3 Claims, No Drawings

(56) References Cited

OTHER PUBLICATIONS

Cuenda et al, "SB203580 is a specific inhibitor of a MAP kinase homologue which is stimulated by cellular stresses and interleukin-1", FEBS Lett., No. 364, 1995, pp. 229-233.

Danham et al, "Inhibition of p38 mitogen activate kinase attenuates the severity of pancreatitis-induced adult respiratory distress syndrome", Crit. Care Med., vol. 28, No. 7, 2000, pp. 2567-2572.

Engel et al, "Leptomycin B-sensitive nuclear export of MAPKAP kinase 2 is regulated by phosphorylation", EMBO J., vol. 17, No. 12, 1998, pp. 3363-3371.

Foster et al, "Potential of p38 Inhibitors in the Treatment of Rheumatoid Arthritis", Drug News Perspect, No. 13(8), 2000, pp. 488-497.

Han et al, "A MAP Kinase Targeted by Endotoxin and Hyperosmolarity in Mammalian Cells", Science, vol. 265, 1994, p. 808.

Jiang et al, "Characterization of the structure and function of a New Mitogen-activated Protein Kinase (p38β)", J. Biol. Chem., vol. 271, No. 30, 1996, pp. 17920-17926.

Jiang et al, "Characterization of the structure and Function of the Fourth Member of p38 Group Mitogen-activated Protein Kinases, p38β", J. Biol. Chem., vol. 272, No. 48, 1997, pp. 30122-30128.

Kotlyarov et al, "MAPKAP kinase 2 is essential for LPS-induced TNF-α biosynthesis", Nat. Cell Biol., vol. 1, 1999, pp. 94-97.

Kumar et al, "P38 Map Kinases: Key Signalling Molecules As Therapeutic Targets for Inflammatory Diseases", Nature Reviews Drug Discovery, vol. 2, 2003, pp. 717-726.

Lebel, "The Addition of Nitrones to Olefins. Fused Bicyclic Isoxazolidines", J. Am. Chem. Soc., vol. 86, 1964, pp. 3759-3767.

Li et al, "The Primary Structure of p38γ: A New Member of p38 Group of MAP Kinases", Biochem. Biophys. Res. Commun., No. 228, 1996, pp. 334-340.

Meng et al, "Structure of Mitogen-activated Protein Kinase-activated Protein (MAPKAP) Kinase 2 Suggests a Bifunctional Switch That Couples Kinase Activiation with Nuclear Export", J. Biol. Chem., vol. 277, No. 40, 2002, pp. 37401-37405.

Mitsunobu et al, "Preparation of Esters of Carboxylic and Phosphoric Acid via Quaternary Phosphonium Salts", Bull. Chem. Soc. Jpn., vol. 40, No. 10, pp. 2380-2382, (1967).

Naldini et al, "Role of Inflammatory Mediators in Angiogenesis", Current Drug Targets, Inflammation & Allergy, No. 4, 2005, pp. 3-8.

Revesz et al, "SAR of 4-Hydroxypiperidine and Hydroxyalkyl Substituted Heterocycles as Novel p38 Map Kinase Inhibitors", Biorg. Med. Chem. Lett., No. 10, 2000, pp. 1261-1264.

Salituro et al, "Inhibitors of p38 MAP Kinase: Therapeutic Intervention in Cytokine-Mediated Diseases", Current Medicinal Chemistry, No. 6, 1999, pp. 807-823.

Schirok et al, "Efficient Regioselective Synthesis of 6-Amino-5-benzoyl-1-Substituted 2(1H)-Pyridinones", J. Org. Chem., No. 70, 2005, pp. 9463-9469.

Underwood et al, "SB 239063 a Potent p38 MAP Kinase Inhibitor, Reduces Inflammatory Cytokine Production, Airways Eosinophil Infiltration, and Persistence", J. Pharmacol. Exp. Ther., vol. 293, No. 1, 2000, pp. 281-288.

Van Roon et al, "Selective Elimination of Synovial Inflammatory Macrophages in Rheumatoid Arthritis by an Fcy Receptor I-Directed Immunotoxin", Arthritis & Rheumatism, vol. 48, No. 5, 2003, pp. 1229-1238.

Yang et al, "Evidence of a central role for p38 map kinase induction of tumor necrosis factor α in pancreatitis-associated pulmonary injury", Surgery, vol. 126, 1999, pp. 216-222.

Wadsworth et al, "RWJ 67657, a Potent, Orally Active Inhibitor of p38 Mitogen-Activated Protein Kinase", J. Pharmacol. Exp. Ther., vol. 291, No. 2, 1999, pp. 680-687.

Waetzig et al, "p38 Mitogen-Activated Protein Kinase Is Activated and Linked to TNF-α Signaling in in Inflammatory Bowel Disease", J. Immunol., No. 168, pp. 5342-5351, (2002).

TERT-BUTYL N-[2-{4-[6-AMINO-5-(2,4-DIFLUOROBENZOYL)-2-OXOPYRIDIN-1(2H)-YL]-3,5-DIFLUOROPHENYL}ETHYL]-L-ALANINATE OR A SALT, HYDRATE OR SOLVATE THEREOF

CROSS-REFERENCE TO RELATED APPLICATIONS

This application is a national phase application under 35 U.S.C. §371 that claims priority to International Application No. PCT/GB2013/052689 filed Oct. 15, 2013, which claims the benefit of priority to Great Britain Patent Application Nos. 1306881.2 filed on Apr. 16, 2013 and 1218640.9 filed on Oct. 17, 2012, all of which are incorporated herein by reference in their entirety.

FIELD OF THE INVENTION

The invention relates to an amino acid ester compound and to compositions comprising the amino acid ester compound. The invention also relates to use of the compound or composition in the inhibition of the p38 MAP kinase enzyme. In addition, the invention relates to an acid produced by hydrolysis of the ester group of the compound of the invention.

BACKGROUND OF THE INVENTION

Inappropriate activation of leukocytes including monocytes, macrophages and neutrophils leading to the production of elevated levels of cytokines such as TNF-α, IL1-β and IL-8, is a feature of the pathogenesis of several inflammatory diseases including rheumatoid arthritis, ulcerative colitis, Crohn's disease, chronic obstructive pulmonary disease (COPD), asthma and psoriasis, and cell proliferative diseases with an inflammatory component. The production of cytokines by inflammatory cells is a result of response to a variety of external stimuli, leading to the activation of a number of intracellular signalling mechanisms. Prominent amongst these is the mitogen-activated protein kinase (MAPK) superfamily consisting of highly conserved signalling kinases that regulate cell growth, differentiation and stress responses. Mammalian cells contain at least three families of MAPKs: the p42/44 extracellular signal-regulated kinase (ERK) MAPKs, c-Jun NH2-terminal kinases (JNKs) and p38 MAPK (also termed p38a/Mpk2/RK/SAPK2a/CSBP1/2). p38 MAPK was first cloned following its identification as a kinase that is tyrosine phosphorylated after stimulation of monocytes by lipopolysaccharide (LPS) [Han et al, Science 1994, 265, 808]. Additional homologues of mammalian p38 have been described and include p38β [Jiang et al, J. Biol. Chem, 1996, 271, 17920], p38γ [Li et al, Biochem. Biophys. Res. Commun., 1996, 228, 334] and p386 [Jiang et al, J. Biol. Chem. 1997, 272, 30122]. While p38α and p38β are ubiquitously expressed, p38γ is restricted primarily to skeletal muscle and p38 δ is predominantly expressed in lung and kidney.

The release of cytokines by host defence cells and the response of leukocytes to cytokines and other pro-inflammatory stresses are to varying extent regulated by p38 MAPK [Cuenda et al, FEBS Lett, 1995, 364, 229-233]. In other cell types, p38 MAPK controls stress responses such as the production of IL-8 by bronchial epithelial cells stimulated by TNF-α and the up-regulation of the cell adhesion molecule ICAM-1 in LPS-stimulated endothelial cells. Upon activation, via dual phosphorylation of a TGY motif by the dual specificity kinases MKK3 and MKK6, p38 MAPK exerts its effects through phosphorylation of transcription factors and other kinases. MAP kinase-activated protein kinase-2 (MAPKAP-K2) has been identified as a target for p38 phosphorylation. It has been demonstrated that mice [Kotlyarov et al, Nat. Cell Biol. 1999, 1, 94-97] lacking MAPKAP-K2 release reduced levels of TNF-α, IL-1β, IL-6, IL-10 and IFN-γ in response to LPS/galactosamine mediated endotoxic shock. The regulation of the levels of these cytokines as well as COX-2 is at the mRNA level. TNF-α levels are regulated through translational control via AU-rich elements of the 3'-UTR of TNF-α mRNA, with MAPKAP-K2 signalling increasing TNF-α mRNA translation. MAPKAP-K2 signalling leads to increased mRNA stability for COX-2, IL-6 and macrophage inflammatory protein. MAPKAP-K2 determines the cellular location of p38 MAPK as well as transducing p38 MAPK signalling, possessing a nuclear localisation signal at its carboxyl terminus and a nuclear export signal as part of its autoinhibitory domain [Engel et al, EMBO J. 1998, 17, 3363-3371]. In stressed cells, MAPKAP-K2 and p38 MAPK migrate to the cytoplasm from the nucleus, this migration only occurring when p38 MAPK is catalytically active. It is believed that this event is driven by the exposure of the MAPKAP-K2 nuclear export signal, as a result of phosphorylation by p38 MAPK [Meng et al, J. Biol. Chem. 2002, 277, 37401-37405]. Additionally p38 MAPK either directly or indirectly leads to the phosphorylation of several transcription factors believed to mediate inflammation, including ATF1/2 (activating transcription factors 1/2), CHOP-10/GADD-153 (growth arrest and DNA damage inducible gene 153), SAP-1 (serum response factor accessory protein-1) and MEF2C (myocyte enhancer factor-2) [Foster et al, Drug News Perspect. 2000, 13, 488-497].

It has been demonstrated in several instances that the inhibition of p38 MAPK activity by small molecules, is useful for the treatment of several disease states mediated by inappropriate cytokine production including rheumatoid arthritis, COPD, asthma and cerebral ischemia. This modality has been the subject of several reviews [Salituro et al, Current Medicinal Chemistry, 1999, 6, 807-823 and Kumar et al, Nature Reviews Drug Discovery 2003, 2, 717-726].

Inhibitors of p38 MAPK have been shown to be efficacious in animal models of rheumatoid arthritis, such as collagen-induced arthritis in rat [Revesz et al, Biorg. Med. Chem. Lett., 2000, 10, 1261-1364] and adjuvant-induced arthritis in rat [Wadsworth et al, J. Pharmacol. Exp. Ther., 1999, 291, 1685-1691]. In murine models of pancreatitis-induced lung injury, pretreatment with a p38 MAPK inhibitor reduced TNF-α release in the airways and pulmonary edema [Denham et al, Crit. Care Med., 2000, 29, 628 and Yang et al, Surgery, 1999, 126, 216]. Inhibition of p38 MAPK before ovalbumin (OVA) challenge in OVA-sensitized mice decreased cytokine and inflammatory cell accumulation in the airways in an allergic airway model of inflammation [Underwood et al, J. Pharmacol. Exp. Ther., 2000, 293, 281]. Increased activity of p38 MAP kinase has been observed in patients suffering from inflammatory bowel disease [Waetzig et al, J. Immunol, 2002, 168, 5432-5351]. p38 MAPK inhibitors have been shown to be efficacious in rat models of cardiac hypertrophy [Behr et al, Circulation, 2001, 104, 1292-1298] and cerebral focal ischemia [Barone et al, J. Pharmacol. Exp. Ther., 2001, 296, 312-321].

WO 2007/129040 and WO 2009/060160 both disclose alpha amino acid esters that are inhibitors of p38 MAP kinase. In the compounds disclosed, the ester group is an ester group which is hydrolysable by one or more intracellular esterase enzymes to a carboxylic acid group; and the substituents on the carbon of the alpha amino acid ester form a side chain, which is the side chain of a natural or non-natural alpha amino acid.

The compounds disclosed are stated to be potent and selective inhibitors of p38 MAPK (p38α, β, γ, and δ) and the isoforms and splice variants thereof especially p38α, p38β and p38β2. The compounds are thus of use in medicine, for example in the treatment and prophylaxis of immune and inflammatory disorders described herein. The compounds are characterised by the presence in the molecule of the amino acid motif or amino acid ester motif —NH—CHR1R2 which is hydrolysable by an intracellular carboxylesterase. The compounds having the lipophilic amino acid ester motif cross the cell membrane, and are hydrolysed to the acid by the intracellular carboxylesterases. The polar hydrolysis product accumulates in the cell since it does not readily cross the cell membrane. Hence the p38 MAP kinase activity of the compounds are prolonged and enhanced within the cell. The compounds of that invention are related to the p38 MAP kinase inhibitors encompassed by the disclosures in International Patent Application WO03076405 but differ in that they have the amino acid ester motif referred to above.

WO 2007/129040 also disclosed that the compounds with which it is concerned include those which selectively accumulate in macrophages. Macrophages are known to play a key role in inflammatory disorders through the release of cytokines in particular TNFα and IL-1 (van Roon et al, Arthritis and Rheumatism, 2003, 1229-1238). In rheumatoid arthritis they are major contributors to the maintenance of joint inflammation and joint destruction. Macrophages are also involved in tumour growth and development (Naldini and Carraro, Curr Drug Targets Inflamm Allergy, 2005, 3-8). Hence agents that selectively target macrophage cell proliferation could be of value in the treatment of cancer and autoimmune disease. Targeting specific cell types would be expected to lead to reduced side-effects. The way in which the esterase motif is linked to the p38 kinase inhibitor determines whether it is hydrolysed, and hence whether or not it accumulates in different cell types. Specifically, macrophages contain the human carboxylesterase hCE-1 whereas other cell types do not. In the general formula (I) of WO 2007/129040, when the nitrogen of the esterase motif R1CH(R2)NH— is not directly linked to a carbonyl (—C(=O)—), ie when Y is not a —C(=O), —C(=O)O— or —C(=O)NR3- radical, the ester will only be hydrolysed by hCE-1 and hence the inhibitors will only accumulate in macrophages. Herein, unless "monocyte" or "monocytes" is specified, the term macrophage or macrophages will be used to denote macrophages (including tumour associated macrophages) and/or monocytes.

WO 2009/060160 discloses a group of specific compounds falling within the general disclosures of WO 2007/129040, but not specifically identified or exemplified therein. The compounds display the macrophage selectivity property discussed above.

SUMMARY OF THE INVENTION

The present inventors have found that the compound tert-butyl N-[2-{4-[6-amino-5-(2,4-difluorobenzoyl)-2-oxopyridin-1(2H)-yl]-3,5-difluorophenyl}ethyl)-L-alaninate is surprisingly good at inhibiting p38 MAP kinase activity. Tests have shown that the IC50 value for ester TNF-α inhibition in human blood is significantly lower than would be expected given the IC50 values for ester TNF-α inhibition in human blood observed for related compounds. Further, tests carried out by the inventors have demonstrated that the bioavailability of the compound of the invention is much higher than would have been predicted from structurally-similar, known compounds.

Accordingly, the present invention provides a compound which is: tert-butyl N-[2-{4-[6-amino-5-(2,4-difluorobenzoyl)-2-oxopyridin-1(2H)-yl]-3,5-difluorophenyl}ethyl)-L-alaninate or a pharmaceutically acceptable salt, hydrate or solvate thereof.

The present invention also provides a pharmaceutical composition comprising the compound together with one or more pharmaceutically acceptable carriers and/or excipients.

In another aspect, the invention provides a compound as defined above or a composition as defined above for use in a method of treatment of the human or animal body by therapy.

The present invention also provides a compound as defined above or a composition as defined above for use in the inhibition of the activity of a p38 MAP kinase enzyme in vitro or in vivo. There is further provided a compound as defined above or a composition as defined above for use in the prevention or treatment of autoimmune or inflammatory disease. Also provided is a compound as defined above or a composition as defined above for use in the treatment of a cell proliferative disease.

In another aspect, the invention provides a method of inhibiting the activity of a p38 MAP kinase enzyme, which method comprises contacting the enzyme with an amount of a compound as defined above or a composition as defined above effective for such inhibition. Also provided is a method of treating or preventing autoimmune or inflammatory disease in a subject, which method comprises administering to said subject an effective amount of a compound as defined above or a composition as defined above. There is further provided a method of treating a cell proliferative disease in a subject, which method comprises administering to said subject an effective amount of a compound as defined above or a composition as defined above. Said treatment may comprise ameliorating or reducing the incidence of the cell proliferative disease.

In yet another aspect, the invention provides the use of a compound as defined above or a composition as defined above in the manufacture of a medicament for inhibiting the activity of a p38 MAP kinase enzyme. Further provided is the use of a compound as defined above or a composition as defined above in the manufacture of a medicament for the prevention or treatment of an autoimmune or inflammatory disease. Also provided is the use of a compound as defined above or a composition as defined above in the manufacture of a medicament for the treatment of a cell proliferative disease.

The invention also provides an agent for inhibiting the activity of a p38 MAP kinase enzyme comprising a compound as defined above or a composition as defined above as active ingredient. The agent is typically for the prevention or treatment of autoimmune or inflammatory disease. It may alternatively be for the treatment of cell proliferative disease.

Also provided by the invention is an acid which is: N-[2-{4-[6-amino-5-(2,4-difluorobenzoyl)-2-oxopyridin-1(2H)-yl]-3,5-difluorophenyl}ethyl)-L-alanine.

DETAILED DESCRIPTION OF THE INVENTION

The invention provides a compound which is: tert-butyl N-[2-{4-[6-amino-5-(2,4-difluorobenzoyl)-2-oxopyridin-1(2H)-yl]-3,5-difluorophenyl}ethyl)-L-alaninate.

The compound of the invention may be prepared in the form of a salt, hydrate or solvate. The invention thus also provides a salt, hydrate or solvate of the compound. Typically, the salt is a pharmaceutically acceptable salt.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, salicylic, glutamic, lactic, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium, barium or magnesium) hydroxides and organic bases such as alkyl amines, aralkyl amines and heterocyclic amines. Examples of suitable organic bases include, but are not limited to, N-methyl-D-glucamine, choline tris(hydroxymethyl)amino-methane, L-arginine, L-lysine, N-ethyl piperidine, dibenzylamine. For a review on suitable salts, see Handbook of Pharmaceutical Salts: Properties, Selection, and Use by Stahl and Wermuth (Wiley-VCH, Weinheim, Germany, 2002).

Suitable salts of the compounds of the invention include those mentioned herein as examples of pharmaceutically acceptable salts.

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

For the avoidance of doubt, the compound of the invention may be used in any tautomeric form.

The compound of the invention includes a chiral centre. The compound is typically in the form of the L-alaninate derivative (i.e. as depicted in Example 1). However, the compound may exist as the D-alaninate derivative or as a mixture of the D- and L-forms. Where a mixture is present, preferably at least 90%, 95% or 99% is present as the L-alaninate derivative.

A suitable scheme and process for the production of the compound of the invention, with reference to the examples section which follows, is discussed below.

The starting materials are typically 4-Chlorophenyl 3-(2,4-difluorophenyl)-3-oxopropanimidothioate hydro-chloride and 2-(4-Amino-3,5-difluorophenyl)ethanol. 2-(4-Amino-3,5-difluorophenyl)ethanol may be prepared using the following scheme, which is analogous to scheme 1 of the examples section:

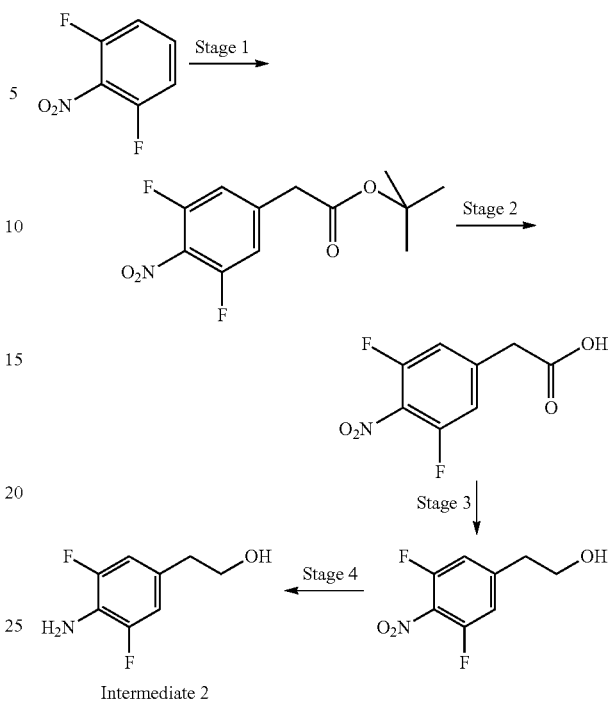

Difluoronitrobenzene is commercially available. Stage 1 requires the addition of a tert-butyl acetate group to the phenyl ring, para to the nitro group. Stage 2 requires the hydrolysis of the ester group to form the corresponding acid. The acid is reduced to a primary alcohol in stage 3. In stage 4 the nitro group is reduced to an amine.

4-Chlorophenyl 3-(2,4-difluorophenyl)-3-oxopropanimidothioate hydro-chloride may be prepared using experimental procedures described in WO 2003076405.

The compound, tert-Butyl N-(2-{4-[6-amino-5-(2,4-difluorobenzoyl)-2-oxopyridin-1(2H)-yl]-3,5-difluorophenyl}ethyl)-L-alaninate may then be synthesised using the following scheme, which is analogous to scheme 2 of the examples section.

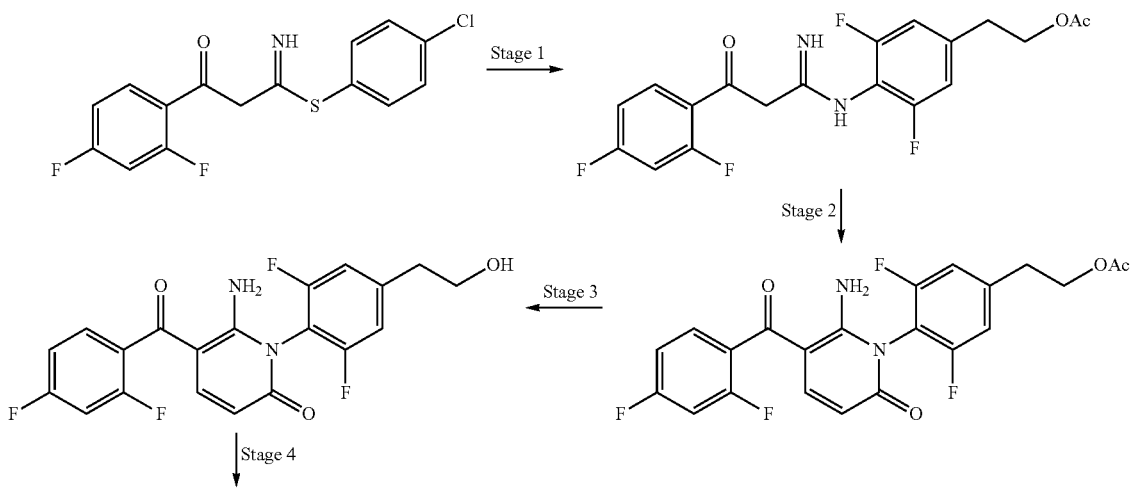

-continued

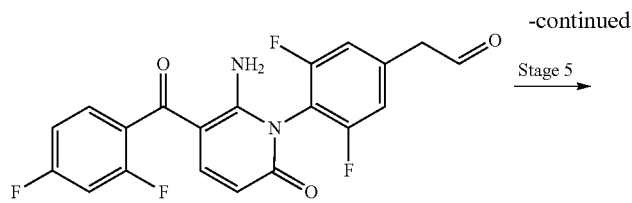

Stage 5

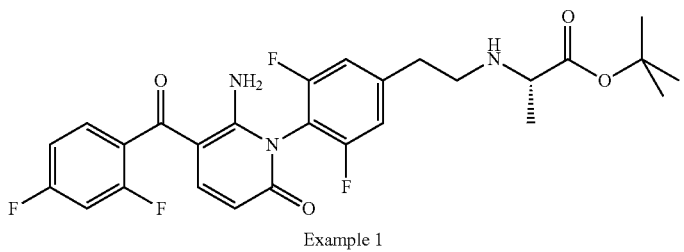

Example 1

In stage 1, the 2-(4-Amino-3,5-difluorophenyl)ethanol and 4-Chlorophenyl difluorophenyl)-3-oxopropanimidothioate hydro-chloride are reacted together to form 2-(4-{[3-(2,4-Difluorophenyl)-3-oxopropanimidoyl]amino}-3,5-difluorophenyl)ethyl acetate. In stage 2, propiolic acid is added to form 2-{4-[6-Amino-5-(2,4-difluorobenzoyl)-2-oxopyridin-1(2H)-yl]-3,5-difluorophenyl}ethyl acetate. In stage 3, the acetate group is hydrolysed to leave an alcohol and in stage 4 the resulting alcohol group is oxidised to an aldehyde. The compound of the invention is then formed in stage 5, by the addition of tert-butyl L-alaninate hydrochloride. Tert-butyl L-alaninate hydrochloride is commercially available.

The invention also provides a pharmaceutical composition comprising the compound together with one or more pharmaceutically acceptable carriers and/or excipients. Said pharmaceutical composition typically contains up to 85 wt % of a compound of the invention. More typically, it contains up to 50 wt % of a compound of the invention. Preferred pharmaceutical compositions are sterile and pyrogen free.

The compound of the invention may be administered in a variety of dosage forms. Thus, they can be administered orally, for example as tablets, troches, capsules, lozenges, aqueous or oily suspensions, dispersible powders or granules. The compounds of the invention may also be administered parenterally, either subcutaneously, intravenously, intramuscularly, intrasternally, transdermally or by infusion techniques. Depending on the vehicle and concentration used, the drug can either be suspended or dissolved in the vehicle. Advantageously, adjuvants such as a local anaesthetic, preservative and buffering agent can be dissolved in the vehicle. The compounds may also be administered as suppositories. The compounds may be administered by inhalation in the form of an aerosol via an inhaler or nebuliser.

A compound of the invention is typically formulated for administration with a pharmaceutically acceptable carrier or diluent. For example, solid oral forms may contain, together with the active compound, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, tragacanth gums, gelatin, syrup, acacia, sorbitol, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in a known manner, for example, by means of mixing, granulating, tabletting, sugar-coating, or film coating processes.

Liquid dispersions for oral administration may be solutions, syrups, emulsions and suspensions. Liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents. The solutions may contain solubilising agents e.g. cyclodextrins or modified cyclodextrins. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. cyclodextrins or modified cyclodextrins, and if desired, a suitable amount of lidocaine hydrochloride.

Solutions for intravenous or infusions may contain as carrier, for example, sterile water and solubilising agents, e.g. cyclodextrins or modified cyclodextrins or preferably they may be in the form of sterile, aqueous, isotonic saline solutions.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

A therapeutically effective amount of a compound of the invention is administered to a subject. It will be understood that the specific dose level for any particular subject will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will usually be determined by clinical trial.

A typical daily dose is up to 50 mg per kg of body weight, for example from 0.001 to 50 mg per kg of body weight, according to the activity of the specific compound, the age, weight and conditions of the subject to be treated, the type and severity of the disease and the frequency and route of administration. Preferably, daily dosage levels are from 0.05 mg to 2 g, preferably from 0.1 mg to 10 mg. The compound of the invention is typically administered to the patient in a non-toxic amount.

The invention also provides a compound as defined herein or a composition as defined herein for use in a method of treatment of the human or animal body by therapy.

The compounds and compositions of the invention have been found to inhibit the activity of a p38 MAP kinase enzyme. The compounds and compositions are therefore useful in the prevention and treatment of diseases and conditions modulated by p38 MAP kinase activity. Diseases and conditions modulated by p38 MAP kinase activity include cell proliferative disease such as cancer and psoriasis, polyglutamine disease such as Huntingdon's disease, neurodegenerative disease such as Alzheimers disease, autoimmune disease such as rheumatoid arthritis, diabetes, haematological disease, inflammatory disease, cardiovascular disease, atherosclerosis, and the inflammatory sequelia of infection. Particular examples are cell proliferative disease, autoimmune disease and inflammatory disease.

Autoimmune disease often has an inflammatory component. Such conditions include acute disseminated alopecia universalise, ANCA positive diseases, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, inflammatory bowel disease, Crohn's disease, diabetes mellitus type 1, Fanconi syndrome, giant cell arteritis, glomerulonephritis, Goodpasture's, syndrome, Grave's disease, Guillain-Barre syndrome, Hashimoto's disease, Henoch-Schönlein purpura, Kawasaki's disease, systemic lupus erythematosus, microscopic colitis, microscopic polyarteritis, mixed connective tissue disease, multiple sclerosis, myasthenia gravis, opsocionus myoclonus syndrome, optic neuritis, Ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

Other inflammatory conditions which may be prevented or treated with the compounds and compositions of the invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensitivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis, primary biliary cirrhosis and primary sclerosing cholangitis.

The compounds and compositions of the invention are useful in the prevention and treatment of inflammatory and autoimmune diseases and conditions. Inflammatory and autoimmune diseases and conditions which can be treated using the compounds and compositions of the invention include rheumatoid arthritis, psoriatic arthritis, Type 1 diabetes, asthma, inflammatory bowel disease, systemic lupus erythematosis, and inflammation accompanying infectious conditions (e.g., sepsis), psoriasis, Crohns disease, ulcerative colitis, chronic obstructive pulmonary disease, multiple sclerosis, atopic dermatitis, and graft versus host disease.

The compounds and compositions of the invention are also useful in the treatment of a cell proliferative disease, for example cancer. Examples of cancers which can be treated include breast cancer, ovarian cancer, lung cancer, pancreatic cancer, hepatic cancer, colon cancer, renal cancer, lymphoma and melanoma. For instance, cancers which may be treated include breast cancer, ovarian cancer, pancreatic cancer, lung cancer, colon cancer, renal cancer, lymphoma or melanoma.

The invention also relates to an acid which is:

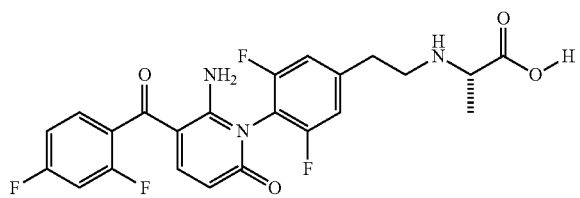

N-[2-{4-[6-amino-5-(2,4-difluorobenzoyl)-2-oxopyridin-1(2H)-yl]-3,5-difluorophenyl}ethyl]-L-alanine.

The acid may be prepared by hydrolysis of the compound of the invention.

As discussed herein, the compound of the invention is macrophage selective. Thus, the ester group of the compound of the invention is hydrolysable by cells containing the human carboxylesterase hCE-1 and not by cells containing hCE-2 or hCE-3. The acid is therefore produced within the cells containing hCE-1 on hydrolysis of the ester group of the compound of the invention and the acid selectively accumulates within such cells.

The present invention is further illustrated in the Examples which follow.

EXAMPLES

The compound of the invention may be prepared according to the following Example.

Abbreviations

CDI=carbonyldiimidazole
DCM=dichloromethane
DMF=dimethylformamide
EtOAc=ethyl acetate
HCl=hydrochloric acid
LCMS=high performance liquid chromatography/mass spectrometry
MeOH=methanol
$MgSO_4$=magnesium sulphate
$Na_2CO_3$=sodium carbonate
$NaHCO_3$=sodium hydrogen carbonate
NMR=nuclear magnetic resonance
STAB=sodium triacetoxyborohydride
THF=tetrahydrofuran
g=gram(s)
mg=milligram(s)
mL=milliliter(s)
mmol=millimole(s)

Commercially available reagents and solvents (HPLC grade) were used without further purification. Solvents were removed using a Buchi rotary evaporator. Microwave irradiation was carried out using a Biotage Initiator™ Eight microwave synthesiser. Purification of compounds by flash chromatography column was performed using silica gel, particle size 40-63 μm (230-400 mesh) obtained from Fluorochem.

$^1$H NMR spectra were recorded on a Bruker 300 MHz AV spectrometer in deuterated solvents. Chemical shifts (d) are in parts per million. Thin-layer chromatography (TLC) analysis was performed with Kieselgel 60 $F_{254}$ (Merck) plates and visualized using UV light.

Analytical HPLC/MS was performed on an Agilent HP1100 LC system using reverse phase Luna C18 columns (3 mm, 50×4.6 mm), gradient 5-95% B (A=water/0.1% Formic acid, B=acetonitrile/0.1% Formic acid) over 2.25 min, flow=2.25 mL/min. UV spectra were recorded at 220 and 254 nm using a G1315B DAD detector. Mass spectra were obtained over the range m/z 150 to 800 on a LC/MSD SL G1956B detector. Data were integrated and reported using ChemStation and ChemStation Data Browser software.

Intermediates

Intermediate 1: 4-Chlorophenyl 3-(2,4-difluorophenyl)-3-oxopropanimidothioate hydro-chloride

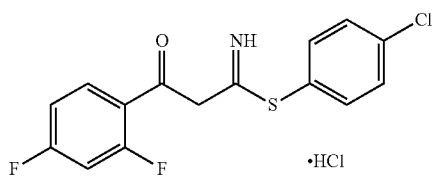 [SMILES: N=C(CC(=O)c1ccc(F)cc1F)Sc1ccc(Cl)cc1 ; Cl]

Intermediate 1 can be prepared using experimental procedures described in WO 2003076405.

Intermediate 2: 2-(4-Amino-3,5-difluorophenyl)ethanol

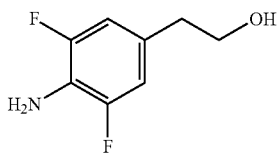 [SMILES: Nc1c(F)cc(CCO)cc1F]

Intermediate 2 was synthesised using the route shown in Scheme 1 below.

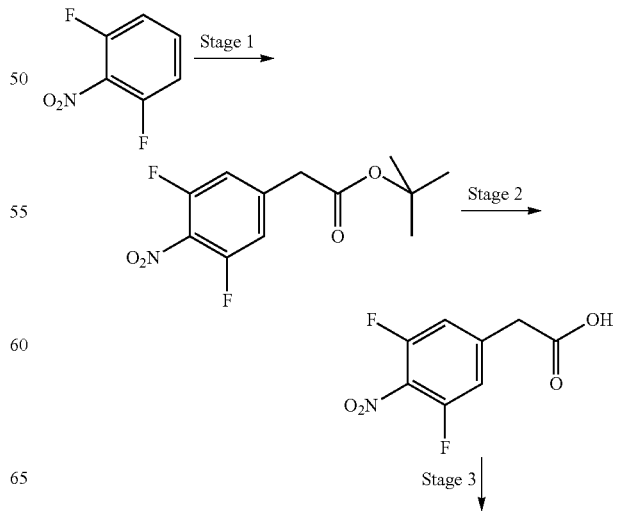

Scheme 1

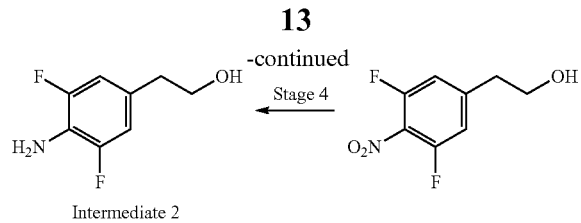

Intermediate 2

Stage 1—tert-Butyl (3,5-difluoro-4-nitrophenyl)acetate

A solution of difluoronitrobenzene (24.96 g, 157 mmol) and tert-butyl chloroacetate (38.0 mL, 267 mmol) in anhydrous DMF (200 mL) was added dropwise over one hour to a cold (−35° C.) suspension of potassium tert-butoxide (61.61 g, 549 mmol) in anhydrous DMF (200 mL) under nitrogen. The reaction mixture was stirred at −35° C. for 1.5 hours, quenched with 2N HCl (240 mL) and extracted with heptanes (4×200 mL). The combined organic extracts were washed with water (3×200 mL), brine (200 mL), dried (MgSO$_4$), filtered and concentrated under reduced pressure to leave a yellow oil. Purification by column chromatography (10% EtOAc in heptanes) afforded a yellow oil (37.64 g). Another two batches (10.00 g and 23.54 g of difluoronitrobenzene) afforded 14.30 g and 31.39 g of product respectively. $^1$H NMR's of all three batches showed a mixture of desired compound and small amounts of unidentified impurities. The 3 batches were combined and used in the next stage without further purification.

$^1$H NMR (300 MHz, CDCl$_3$) 7.05 (2H, d, J=8.5 Hz), 3.56 (2H, s), 1.46 (9H, s).

Stage 2—(3,5-Difluoro-4-nitrophenyl)acetic acid

Trifluoroacetic acid (150 mL) was added dropwise over 20 minutes to a cold (0° C.) solution of tert-butyl (3,5-difluoro-4-nitrophenyl)acetate (83.33 g, 305 mmol) in DCM (300 mL). On completion of the addition, the reaction mixture was allowed to warm to room temperature and stirred for 3 hours. The reaction mixture was concentrated under reduced pressure to leave a sticky brown solid. Trituration with heptanes afforded the title compound as a yellow solid (53.29 g, 67% yield over two steps).

$^1$H NMR (300 MHz, CDCl$_3$) 7.08 (2H, d, J=8.5 Hz), 3.74 (2H, s), —CO$_2$H not visible.

Stage 3—2-(3,5-Difluoro-4-nitrophenyl)ethanol

Borane-dimethyl sulfide complex (35 mL, 368 mmol) was added dropwise over 20 minutes to a cold (0° C.) solution of (3,5-difluoro-4-nitrophenyl)acetic acid (53.29 g, 245 mmol) in anhydrous THF (500 mL) under nitrogen. Upon completion of the addition, the reaction mixture was allowed to warm to room temperature, stirred for 16 hours, cooled to 0° C., carefully quenched with MeOH (300 mL) and concentrated under reduced pressure to leave a brown oil. Purification by dry flash chromatography (60-80% EtOAc in heptanes) afforded the title compound as an orange oil (38.90 g, 78% yield).

$^1$H NMR (300 MHz, CDCl$_3$) 7.01 (2H, d, J=8.7 Hz), 3.93 (2H, t, J=6.2 Hz), 2.92 (2H, t, J=6.2 Hz), 2.34 (1H, br s).

Stage 4—2-(4-Amino-3,5-difluorophenyl)ethanol 2-(3,5-Difluoro-4-nitrophenyl)ethanol (38.90 g, 191 mmol) was dissolved in EtOAc (250 mL). The reaction vessel was evacuated and filled with nitrogen three times. Palladium on carbon (10 wt %, 4.00 g) was added and the vessel was evacuated and filled with nitrogen three times. Finally, the vessel was evacuated and filled with hydrogen and fitted with a balloon containing hydrogen. After, stirring at room temperature under hydrogen for 15 hours, the hydrogen balloon was refilled and the mixture stirred for an additional 25 hours. The reaction mixture was filtered through Celite® and the filtrate was concentrated under reduced pressure to leave a brown oil. Purification by dry flash chromatography (50% EtOAc in heptanes) afforded the title compound as a beige solid (20.70 g, 62% yield).

$^1$H NMR (300 MHz, CDCl$_3$) 6.73-6.70 (2H, m), 3.81 (2H, t, J=6.4 Hz), 2.75 (2H, t, J=6.4 Hz), —O$\underline{\text{H}}$ and —N$\underline{\text{H}}_2$ not visible.

Example 1 tert-Butyl N-(2-{4-[6-amino-5-(2,4-difluorobenzoyl)-2-oxopyridin-1(2H)-yl]-3,5-difluorophenyl}ethyl)-L-alaninate

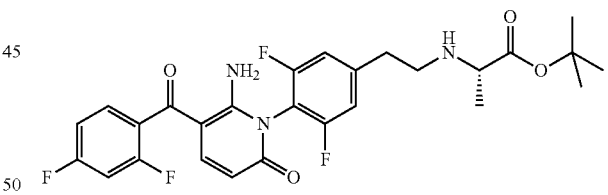

Example 1 was synthesised using the route shown in Scheme 2 below.

Scheme 2

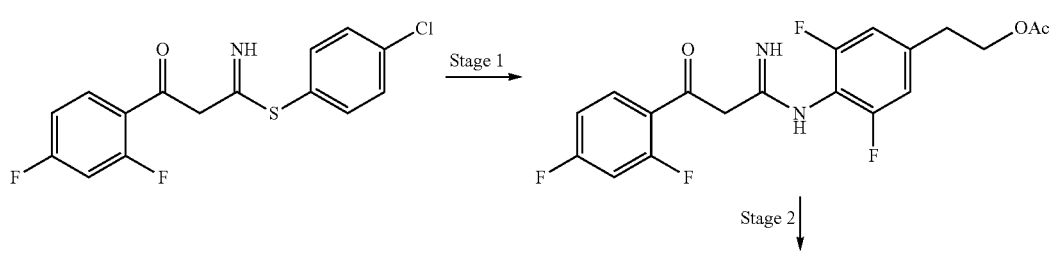

Stage 2

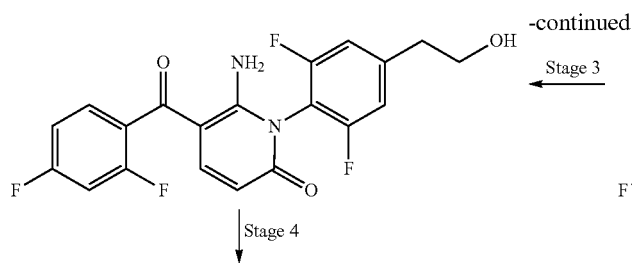
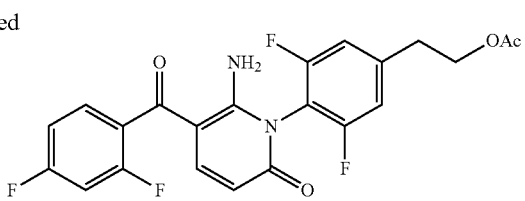
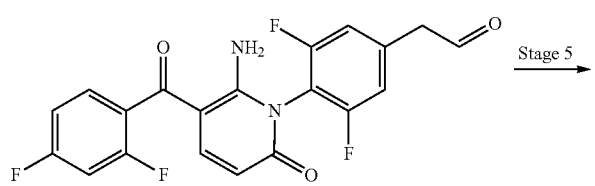
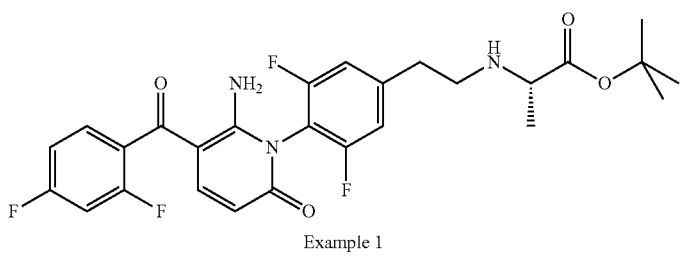

Example 1

Stage 1—2-(4-{[3-(2,4-Difluorophenyl)-3-oxopropanimidoyl]amino}-3,5-difluorophenyl)ethyl acetate 2-(4-Amino-3,5-difluorophenyl)ethanol (20.71 g, 120 mmol) was added to a solution of 4-chlorophenyl 3-(2,4-difluorophenyl)-3-oxopropanimidothioate hydrochloride (41.26 g, 114 mmol) in glacial acetic acid (400 mL). The reaction mixture was stirred at 80° C. for 2.5 hours and acetic anhydride (21 mL, 228 mmol) was added. After an additional 45 minutes at 80° C., the reaction mixture was allowed to cool to room temperature and concentrated under reduced pressure to leave a brown oil. Trituration with EtOAc afforded a beige solid, which was washed with diethyl ether. The solid was taken up in a saturated aqueous solution of NaHCO$_3$ and vigorously stirred for 30 minutes. A solid was collected by filtration, washed with water and allowed to dry under reduced pressure to afford the title compound as a beige solid (23.36 g, 52% yield).

LCMS: m/z 397 [M+H]$^+$.

Stage 2—2-{4-[6-Amino-5-(2,4-difluorobenzoyl)-2-oxopyridin-1(2H)-yl]-3,5-difluorophenyl}ethyl acetate Propiolic acid (5.4 mL, 88 mmol) was added dropwise over 5 minutes to a cold (0° C.) solution of CDI (14.27 g, 88 mmol) in anhydrous THF (400 mL) under nitrogen. After completion of the addition, the reaction mixture was allowed to warm to room temperature and stirred for one hour. A solution of 2-(4-{[3-(2,4-difluorophenyl)-3-oxopropanimidoyl]amino}-3,5-difluoro-phenyl)ethyl acetate (23.26 g, 59 mmol) in anhydrous THF (200 mL) was added and the reaction mixture was stirred at reflux for 6.5 hours. The reaction mixture was allowed to cool to room temperature and left standing for 16.5 hours. Propiolic acid (5.4 mL, 88 mL), CDI (14.27 g, 88 mmol) and THF (200 mL) were treated as described above and added to the reaction mixture, which was subsequently stirred at reflux for an additional 6 hours. The reaction mixture was then allowed to cool to room temperature and concentrated under reduced pressure to leave a brown oil. Purification by dry flash chromatography (5% MeOH in DCM) gave a dark brown solid, which was further purified by trituration with EtOAc to afford the title compound as a yellow solid (7.45 g, 28% yield).

LCMS: m/z 449 [M+H]$^+$ and 471 [M+Na]$^+$.

Stage 3—6-Amino-5-(2,4-difluorobenzoyl)-1-[2,6-difluoro-4-(2-hydroxyethyl)phenyl]pyridin-2(1H)-one 2-{4-[6-Amino-5-(2,4-difluorobenzoyl)-2-oxopyridin-1(2H)-yl]-3,5-difluorophenyl}ethyl acetate (7.45 g, 17 mmol) was suspended in 6N HCl (80 mL) and the reaction mixture was refluxed for 21.5 hours. A solid was collected by filtration, taken up in a saturated aqueous solution of NaHCO$_3$ (200 mL) and vigorously stirred for 30 minutes. A solid was collected by filtration, washed with water and dried in a vacuum oven (40° C.) to afford the title compound as a beige solid.

LCMS: m/z 407 [M+H]$^+$ and 429 [M+Na]$^+$.

$^1$H NMR (300 MHz, DMSO-d$_6$) 7.57 (1H, td, J=6.6, 8.3 Hz), 7.41 (1H, td, J=2.4, 9.7 Hz), 7.37-7.29 (3H, m), 7.23 (1H, td, J=2.3, 8.5 Hz), 5.74 (1H, d, J=9.8 Hz), 4.78 (1H, t, J=5.1 Hz), 3.76-3.70 (2H, m), 2.86 (2H, t, J=6.7 Hz), —NH$_2$ not visible

Stage 4—{4-[6-Amino-5-(2,4-difluorobenzoyl)-2-oxopyridin-1(2H)-yl]-3,5-difluorophenyl}-acetaldehyde Dess-Martin periodinane (1.03 g, 2.4 mmol) was added to a suspension of 6-amino-5-(2,4-difluorobenzoyl)-1-[2,6-difluoro-4-(2-hydroxyethyl)phenyl]pyridin-2(1H)-one (823 mg, 2.0 mmol) in DCM (20 mL). The reaction mixture was stirred at room temperature for 2 hours, quenched with a saturated aqueous solution of NaHCO$_3$ (10 mL) and a saturated aqueous solution of sodium thiosulfate (10 mL) and vigorously stirred for 30 minutes. The aqueous layer was separated and further extracted with DCM (2×20 mL). The combined organic extracts were dried (MgSO$_4$), filtered and concentrated under reduced pressure to afford the title compound as a pale brown solid (819 mg). This was used without further purification in the next stage.

Stage 5—tert-Butyl N-(2-{4-[6-amino-5-(2,4-difluorobenzoyl)-2-oxopyridin-1(2H)-yl]-3,5-difluorophenyl}ethyl)-L-alaninate tert-Butyl L-alaninate hydrochloride (552 mg, 3.0 mmol) and STAB (1.29 g, 6.1 mmol) were added to a solution of {4-[6-amino-5-(2,4-difluorobenzoyl)-2-oxopyridin-1(2H)-yl]-3,5-difluorophenyl}-acetaldehyde (819 mg, 2.0 mmol). The reaction mixture was stirred at room temperature for 3.5 hours, quenched with a saturated aqueous solution of Na$_2$CO$_3$ (20 mL) and vigorously stirred for 20 minutes. The aqueous layer was separated and further extracted with EtOAc (2×20 mL). The combined organic extracts were washed with brine (20 mL), dried (MgSO$_4$), filtered and concentrated under reduced pressure to leave a yellow oil. Purification by column chromatography (5% MeOH in DCM) afforded the title compound as a pale yellow solid (492 mg, 78% yield over two steps).

LCMS: purity 98%, m/z 534 [M+H]$^+$.

$^1$H NMR (300 MHz, DMSO-d$_6$) 7.58 (1H, td, J=6.8, 8.3 Hz), 7.41 (1H, td, J=2.3, 9.8 Hz), 7.37-7.30 (3H, m), 7.23 (1H, td, J=2.3, 8.5 Hz), 5.74 (1H, d, J=9.8 Hz), 3.20 (1H, d, J=7.0 Hz), 2.89-2.70 (4H, m), 1.42 (9H, s), 1.16 (3H, d, J=7.0 Hz), —NH$_2$ and —NH— not visible Measurement of Biological Activities p38 MAP Kinase Activity The ability of compounds to inhibit p38 MAP a Kinase activity was measured in an assay performed by Upstate (Dundee UK). In a final reaction volume of 25 μL, p38 MAP Kinase a (5-10 mU) is incubated with 25 mM Tris pH 7.5, 0.002 mMEGTA, 0.33 mg/mL myelin basic protein, 10 mM MgAcetate and [g-33p-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

Duplicate data points are generated from a 1/3 log dilution series of a stock solution in DMSO. Nine dilutions steps are made from a top concentration of 10 μM, and a 'no compound' blank is included. The standard radiometric filter-binding assay is performed at an ATP concentration at, or close to, the Km. Data from scintillation counts are collected and subjected to free-fit analysis by Prism software. From the curve generated, the concentration giving 50% inhibition is determined and reported.

LPS-Stimulation of THP-1 Cells

THP-1 cells were plated in 100 μl at a density of 4×10$^4$ cells/well in V-bottomed 96 well tissue culture treated plates and incubated at 37° C. in 5% CO$_2$ for 16 hrs. 2 hrs after the addition of the inhibitor in 100 μl of tissue culture media, the cells were stimulated with LPS (E coli strain 005:B5, Sigma) at a final concentration of 1 μg/ml and incubated at 37° C. in 5% CO$_2$ for 6 hrs. TNF-α levels were measured from cell-free supernatants by sandwich ELISA (R&D Systems #QTA00B).

LPS-Stimulation of Human Whole Blood

Whole blood was taken by venous puncture using heparinised vacutainers (Becton Dickinson) and diluted in an equal volume of RPMI1640 tissue culture media (Sigma). 100 μl was plated in V-bottomed 96 well tissue culture treated plates. 2 hrs after the addition of the inhibitor in 100 μl of RPMI1640 media, the blood was stimulated with LPS (E coli strain 005:B5, Sigma) at a final concentration of 100 ng/ml and incubated at 37° C. in 5% CO$_2$ for 6 hrs. TNF-α levels were measured from cell-free supernatants by sandwich ELISA (R&D Systems #QTA00B).

Plasma Exposure in Mice

The compounds were formulated in 8% DMSO, 92% 11.25% hydroxypropyl-β-cyclodextrin in water using the following procedure: the compounds were fully dissolved in 100% DMSO and then the hydroxypropyl-β-cyclodextrin solution added. The fine precipitate formed was re-dissolved by the addition of aqueous HCl and the pH adjusted to 4 with aqueous sodium hydroxide.

Each compound was administered orally at 10 mg/kg, in a total dose volume of 5 ml/kg, to male CD1 mice (25-20 g). Three mice were used for each time point. Blood samples were taken at the following time points: 5, 15, 30, 60, 120, 240 and 360 minutes, by terminal cardiac puncture, under halothane/isofluorane anaesthesia. Blood samples were collected into pre-chilled tubes containing NaF/EDTA and mixed. Samples were spun at 7-7.5×g for 2 minutes. The plasma was aspirated and frozen.

Plasma samples were prepared by precipitation of protein using three volumes of acetonitrile containing the internal standard. The supernatants were analysed by LCMS (Sciex API 3000, HP1100 binary pump, CTC PAL). The chromatography was based on an Acentis C8 (50×2.1 mm) column and a mobile phase of 5-95% acetonitrile in water/0.1% formic acid.

Exposure (AUC) was calculated from the plasma concentration versus time profile using PK Solutions 2.0 (Summit Research Services, Montrose, Colo.).

TABLE 1

Biological Activity of the Compound of the Invention and Structurally Related Compounds
Columns A to D provide data for the following:
A—ester enzyme assay (p38 kinase A (invitrogen)), IC50 (nM);
B—acid enzyme assay (p38 kinase A (invitrogen)), IC50 (nM);
C—ester TNF-alpha inhibition (THP-1 cells), IC50 (nM); and
D—ester TNF-alpha inhibition (human whole blood), IC50 (nM).

| Chemical Structure | Name | A | B | C | D |
|---|---|---|---|---|---|
| 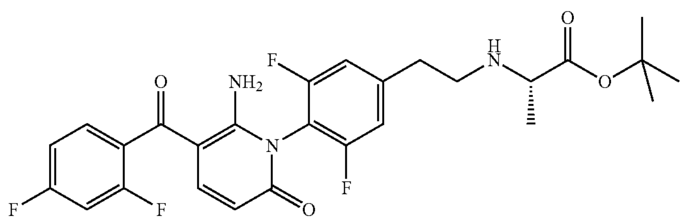 [SMILES: C[C@H](NCCc1cc(F)c(-n2c(N)c(C(=O)c3ccc(F)cc3F)ccc2=O)c(F)c1)C(=O)OC(C)(C)C] | tert-Butyl N-(2-{4-[6-amino-5-(2,4-difluoro-benzoyl)-2-oxopyridin-1(2H)-yl]-3,5-difluorophenyl}ethyl)-L-alaninate | 12 | 1 | 1.6 | 26 |
| 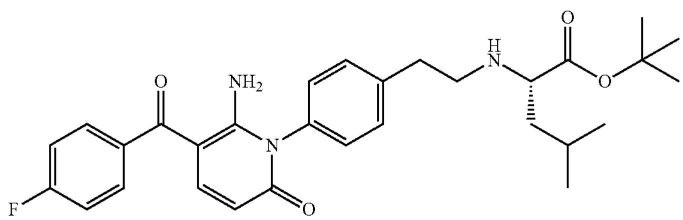 [SMILES: CC(C)C[C@H](NCCc1ccc(-n2c(N)c(C(=O)c3ccc(F)cc3)ccc2=O)cc1)C(=O)OC(C)(C)C] | tert-Butyl N-[2-(4-{6-amino-5-[(4-fluoro-phenyl)carbonyl]-2-oxopyridin-1(2H)-yl}phenyl)ethyl]-L-leucinate | 724 | 118 | 19.0 | 947 |
| 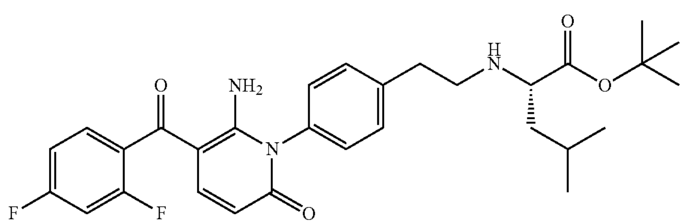 [SMILES: CC(C)C[C@H](NCCc1ccc(-n2c(N)c(C(=O)c3ccc(F)cc3F)ccc2=O)cc1)C(=O)OC(C)(C)C] | tert-Butyl N-[2-(4-{6-amino-5-[(2,4-difluoro-phenyl)carbonyl]-2-oxopyridin-1(2H)-yl}phenyl)ethyl]-L-leucinate | 330 | 58 | 2.4 | 638 |
| 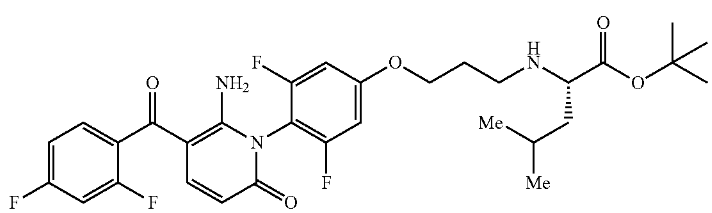 [SMILES: CC(C)C[C@H](NCCCOc1cc(F)c(-n2c(N)c(C(=O)c3ccc(F)cc3F)ccc2=O)c(F)c1)C(=O)OC(C)(C)C] | tert-Butyl (S)-2-(3-{4-[6-Amino-5-(2,4-difluoro benzoyl)-2-oxo-2H-pyridin-1-yl]-3,5-difluoro-phenoxy}propyl-amino)-4-methyl pentanoate | | | 76.1 | 4274 |
| 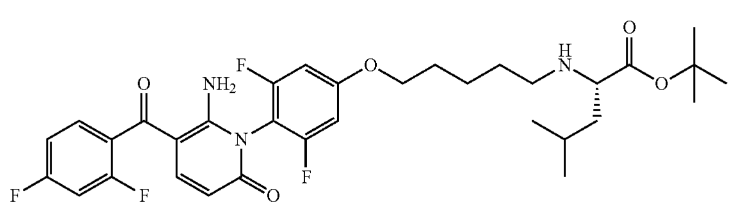 [SMILES: CC(C)C[C@H](NCCCCCOc1cc(F)c(-n2c(N)c(C(=O)c3ccc(F)cc3F)ccc2=O)c(F)c1)C(=O)OC(C)(C)C] | tert-Butyl N-(5-{4-[6-amino-5-(2,4-difluoro-benzoyl)-2-oxopyridin-1(2H)-yl]-3,5-difluorophenoxy}pentyl)-L-leucinate | 73 | 2 | 29.0 | 1247 |
| 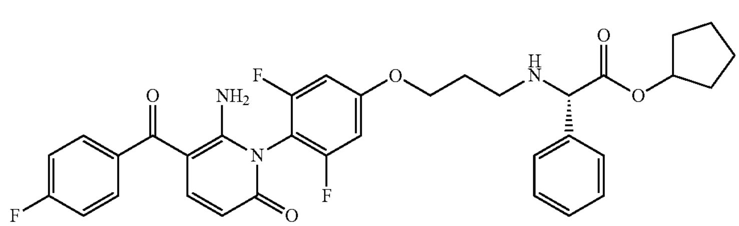 [SMILES: Nc1c(C(=O)c2ccc(F)cc2)ccc(=O)n1-c1c(F)cc(OCCCN[C@H](C(=O)OC2CCCC2)c2ccccc2)cc1F] | Cyclopentyl (S)-(3-{4-[6-Amino-5-(4-fluorobenzoyl)-2-oxo-2H-pyridin-1-yl]-3,5-difluoro-phenoxy}propylamino) phenylacetate | | | 38.0 | |

TABLE 1-continued

Biological Activity of the Compound of the Invention and Structurally Related Compounds
Columns A to D provide data for the following:
A—ester enzyme assay (p38 kinase A (invitrogen)), IC50 (nM);
B—acid enzyme assay (p38 kinase A (invitrogen)), IC50 (nM);
C—ester TNF-alpha inhibition (THP-1 cells), IC50 (nM); and
D—ester TNF-alpha inhibition (human whole blood), IC50 (nM).

| Chemical Structure | Name | A | B | C | D |
|---|---|---|---|---|---|
| 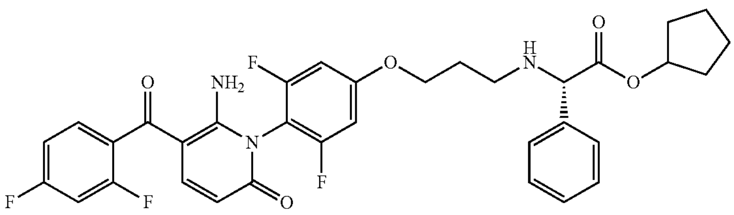 [SMILES: Nc1c(C(=O)c2ccc(F)cc2F)ccc(=O)n1-c1c(F)cc(OCCCN[C@H](C(=O)OC2CCCC2)c2ccccc2)cc1F] | Cyclopentyl (S)-(3-{4-[6-Amino-5-(2,4-difluoro benzoyl)-2-oxo-2H-pyridin-1-yl]-3,5-difluoro-phenoxy}propylamino) phenyl acetate | | | 5.3 | 508 |
| 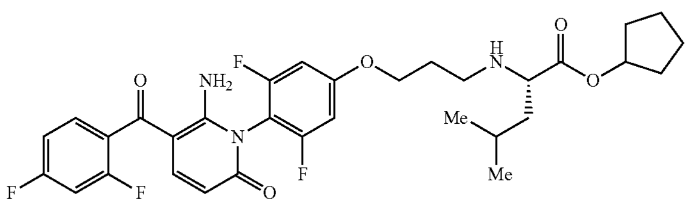 [SMILES: CC(C)C[C@H](NCCCOc1cc(F)c(-n2c(N)c(C(=O)c3ccc(F)cc3F)ccc2=O)c(F)c1)C(=O)OC1CCCC1] | Cyclopentyl (S)-2-(3-{4-[6-Amino-5-(2,4-difluoro benzoyl)-2-oxo-2H-pyridin-1-yl]-3,5-difluoro-phenoxy}propyl-amino)-4-methyl pentanoate | | | 10.7 | 594 |
| 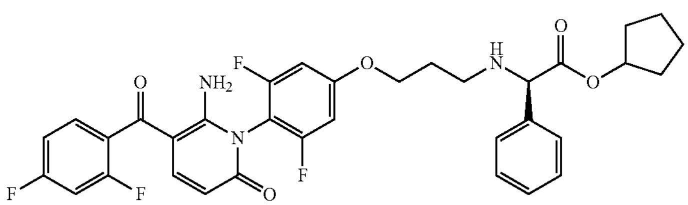 [SMILES: Nc1c(C(=O)c2ccc(F)cc2F)ccc(=O)n1-c1c(F)cc(OCCCN[C@@H](C(=O)OC2CCCC2)c2ccccc2)cc1F] | Cyclopentyl (2R)-[(3-{4-[6-amino-5-(2,4-difluorobenzoyl)-2-oxopyridin-1(2H)-yl]-3,5-difluorophenoxy}propyl)amino](phenyl)acetate | | | 6.0 | |
| 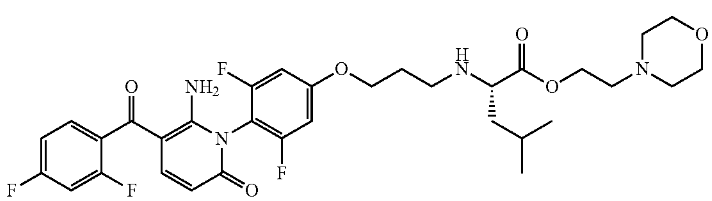 [SMILES: CC(C)C[C@H](NCCCOc1cc(F)c(-n2c(N)c(C(=O)c3ccc(F)cc3F)ccc2=O)c(F)c1)C(=O)OCCN1CCOCC1] | 2-Morpholin-4-ylethyl N-(3-{4-[6-amino-5-(2,4-difluorobenzoyl)-2-oxopyridin-1(2H)-yl]-3,5-difluoro-phenoxy}propyl)-L-leucinate | | | 0.4 | 935 |
| 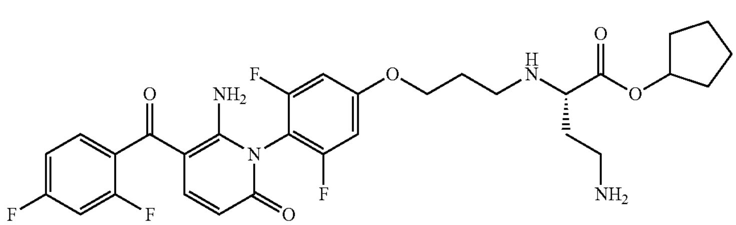 [SMILES: NCC[C@H](NCCCOc1cc(F)c(-n2c(N)c(C(=O)c3ccc(F)cc3F)ccc2=O)c(F)c1)C(=O)OC1CCCC1] | Cyclopentyl (2S)-4-amino-2-[(3-{4-[6-amino-5-(2,4-difluoro-benzoyl)-2-oxopyridin-1(2H)-yl]-3,5-difluoro-phenoxy}propyl)amino]butanoate | 1 | 5 | 22.0 | 479 |
| 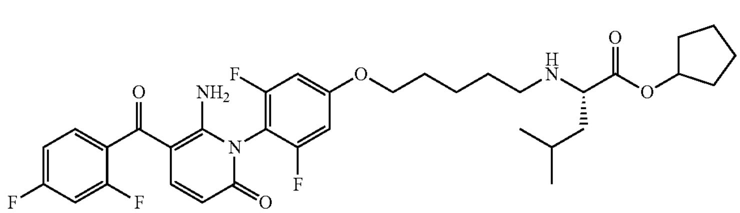 [SMILES: CC(C)C[C@H](NCCCCCOc1cc(F)c(-n2c(N)c(C(=O)c3ccc(F)cc3F)ccc2=O)c(F)c1)C(=O)OC1CCCC1] | Cyclopentyl N-(5-{4-[6-amino-5-(2,4-difluorobenzoyl)-2-oxopyridin-1(2H)-yl]-3,5-difluorophenoxy}pentyl)-L-leucinate | 81 | 2 | 4.2 | 179 |

TABLE 1-continued

Biological Activity of the Compound of the Invention and Structurally Related Compounds
Columns A to D provide data for the following:
A—ester enzyme assay (p38 kinase A (invitrogen)), IC50 (nM);
B—acid enzyme assay (p38 kinase A (invitrogen)), IC50 (nM);
C—ester TNF-alpha inhibition (THP-1 cells), IC50 (nM); and
D—ester TNF-alpha inhibition (human whole blood), IC50 (nM).

| Chemical Structure | Name | A | B | C | D |
|---|---|---|---|---|---|
| 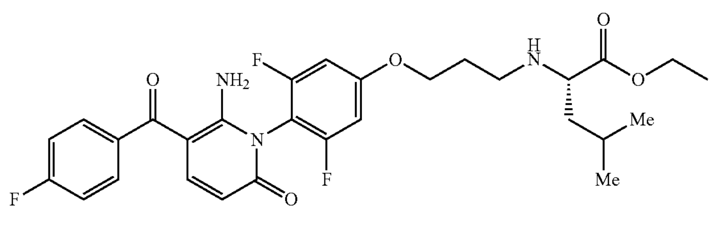 [SMILES: CCOC(=O)[C@H](CC(C)C)NCCCOc1cc(F)c(-n2c(N)c(C(=O)c3ccc(F)cc3)ccc2=O)c(F)c1] | Ethyl N-(3-{4-[6-amino-5-(4-fluoro-benzoyl)-2-oxopyridin-1(2H)-yl]-3,5-difluorophenoxy}propyl)-L-leucinate | 28 | | 8.6 | |
| 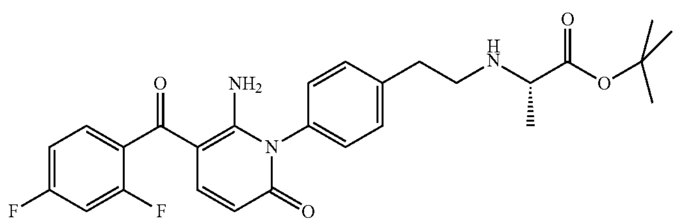 [SMILES: C[C@H](NCCc1ccc(-n2c(N)c(C(=O)c3ccc(F)cc3F)ccc2=O)cc1)C(=O)OC(C)(C)C] | tert-butyl N-[2-(4-{6-amino-5-[(2,4-difluoro-phenyl)carbonyl]-2-oxopyridin-1(2H)-yl}phenyl)ethyl]-L-alaninate | 58 | 58 | 2.8 | 195 |
| 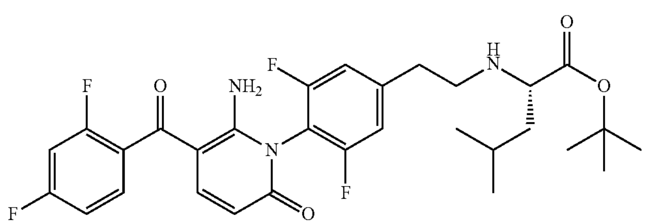 [SMILES: CC(C)C[C@H](NCCc1cc(F)c(-n2c(N)c(C(=O)c3ccc(F)cc3F)ccc2=O)c(F)c1)C(=O)OC(C)(C)C] | tert-butyl N-(2-{4-[6-amino-5-(2,4-difluoro-benzoyl)-2-oxopyridin-1(2H)-yl]-3,5-difluorophenyl}ethyl)-L-leucinate | 120 | 1 | 3.0 | 191 |
| 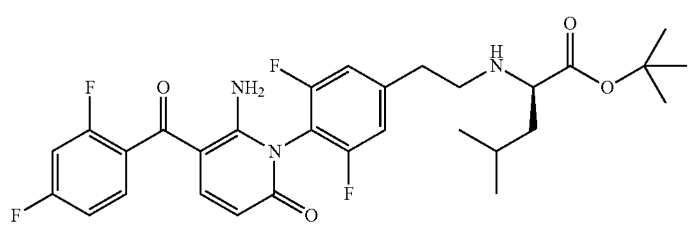 [SMILES: CC(C)C[C@@H](NCCc1cc(F)c(-n2c(N)c(C(=O)c3ccc(F)cc3F)ccc2=O)c(F)c1)C(=O)OC(C)(C)C] | tert-butyl N-(2-{4-[6-amino-5-(2,4-difluoro-benzoyl)-2-oxopyridin-1(2H)-yl]-3,5-difluoro-phenyl}ethyl)-D-leucinate | 167 | 2 | 81.0 | 0% @ 10 μm |
| 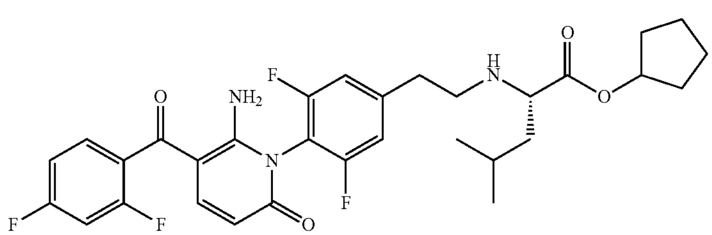 [SMILES: CC(C)C[C@H](NCCc1cc(F)c(-n2c(N)c(C(=O)c3ccc(F)cc3F)ccc2=O)c(F)c1)C(=O)OC1CCCC1] | cyclopentyl N-(2-{4-[6-amino-5-(2,4-difluoro-benzoyl)-2-oxopyridin-1(2H)-yl]-3,5-difluoro-phenyl}ethyl)-L-leucinate | 231 | 1 | 0.5 | 54 |
| 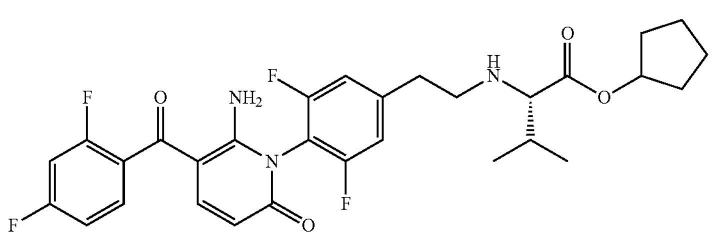 [SMILES: CC(C)[C@H](NCCc1cc(F)c(-n2c(N)c(C(=O)c3ccc(F)cc3F)ccc2=O)c(F)c1)C(=O)OC1CCCC1] | Cyclopentyl N-[2-(4-{6-amino-5-[(2,4-difluoro-phenyl)carbonyl]-2-oxopyridin-1(2H)-yl}-3,5 difluorophenyl)ethyl]-L-valinate | 22 | | 8.4 | 5184 |

TABLE 1-continued

Biological Activity of the Compound of the Invention and Structurally Related Compounds
Columns A to D provide data for the following:
A—ester enzyme assay (p38 kinase A (invitrogen)), IC50 (nM);
B—acid enzyme assay (p38 kinase A (invitrogen)), IC50 (nM);
C—ester TNF-alpha inhibition (THP-1 cells), IC50 (nM); and
D—ester TNF-alpha inhibition (human whole blood), IC50 (nM).

| Chemical Structure | Name | A | B | C | D |
|---|---|---|---|---|---|
| | Cyclopentyl N-[2-(4-{6-amino-5-[(2,4-difluorophenyl)carbonyl]-2-oxopyridin-1(2H)-yl}phenyl)ethyl]-L-threoninate | 68 | 56 | 1.8 | 1198 |
| | Cyclopentyl N-(2-{4-[6-amino-5-(4-fluorobenzoyl)-2-oxopyridin-1(2H)-yl]-3,5-difluorophenyl}ethyl)-L-leucinate | 12 | 1 | 0.9 | 190 |
| | Cyclopentyl (2S)-[(2-{4-[6-amino-5-(2,4-difluorobenzoyl)-2-oxopyridin-1(2H)-yl]-3,5-difluorophenyl}ethyl)amino](phenyl)acetate | 65 | 1 | 0.5 | 148 |
| | tert-butyl (2S)-[(2-{4-[6-amino-5-(2,4-difluorobenzoyl)-2-oxopyridin-1(2H)-yl]-3,5-difluorophenyl}ethyl)amino](phenyl)acetate | 44 | 1 | 2.0 | 779 |
| | Cyclopentyl N-(2-{4-[6-amino-5-(2,4-difluorobenzoyl)-2-oxopyridin-1(2H)-yl]-3,5-difluorophenyl}ethyl)-O-tert-butyl-L-serinate | 57 | 1 | 5.7 | 1295 |
| | tert-butyl N-(2-{4-[6-amino-5-(2,4-difluorobenzoyl)-2-oxopyridin-1(2H)-yl]-3,5-difluorophenyl}ethyl)-O-tert-butyl-L-serinate | 72 | 1 | 83.0 | |

TABLE 1-continued

Biological Activity of the Compound of the Invention and Structurally Related Compounds
Columns A to D provide data for the following:
A—ester enzyme assay (p38 kinase A (invitrogen)), IC50 (nM);
B—acid enzyme assay (p38 kinase A (invitrogen)), IC50 (nM);
C—ester TNF-alpha inhibition (THP-1 cells), IC50 (nM); and
D—ester TNF-alpha inhibition (human whole blood), IC50 (nM).

| Chemical Structure | Name | A | B | C | D |
|---|---|---|---|---|---|
| 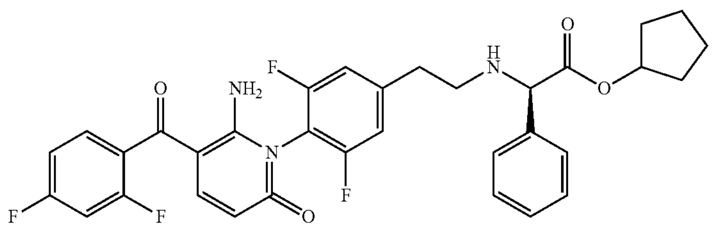 | Cyclopentyl (2R)-[(2-{4-[6-amino-5-(2,4-difluoro-benzoyl)-2-oxopyridin-1(2H)-yl]-3,5-difluorophenyl}ethyl)amino](phenyl)acetate | 47 | | 21.0 | 4108 |

TABLE 2

Plasma exposure in mice

| Chemical Structure | Name | po 10 mg/kg $AUC_{0-t}$ (ng/mL · h) |
|---|---|---|
| 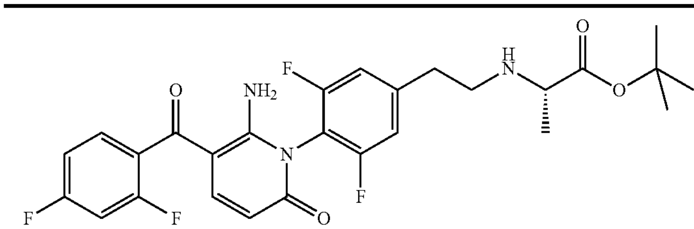 | tert-Butyl N-(2-{4-[6-amino-5-(2,4-difluorobenzoyl)-2-oxopyridin-1(2H)-yl]-3,5-difluorophenyl}ethyl)-L-alaninate | 102 |
| 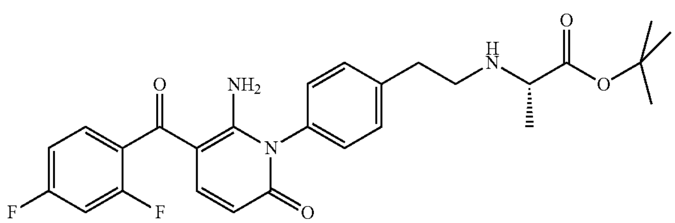 [SMILES: C[C@H](NCCc1ccc(-n2c(N)c(C(=O)c3ccc(F)cc3F)ccc2=O)cc1)C(=O)OC(C)(C)C] | tert-butyl N-[2-(4-{6-amino-5-[(2,4-difluorophenyl)carbonyl]-2-oxopyridin-1(2H)-yl}phenyl)ethyl]-L-alaninate | 0 |
| 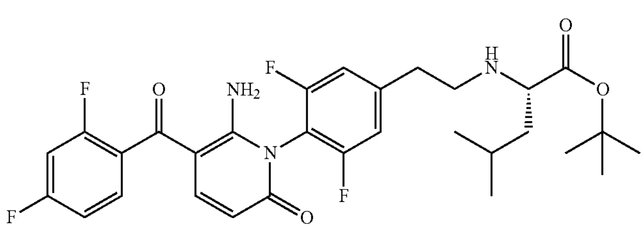 [SMILES: CC(C)C[C@H](NCCc1cc(F)c(-n2c(N)c(C(=O)c3ccc(F)cc3F)ccc2=O)c(F)c1)C(=O)OC(C)(C)C] | tert-butyl N-(2-{4-[6-amino-5-(2,4-difluorobenzoyl)-2-oxopyridin-1(2H)-yl]-3,5-difluorophenyl}ethyl)-L-leucinate | 75 |
| 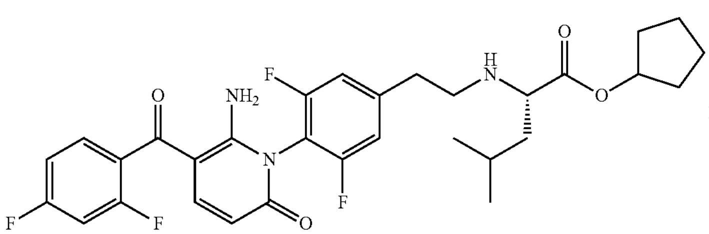 [SMILES: CC(C)C[C@H](NCCc1cc(F)c(-n2c(N)c(C(=O)c3ccc(F)cc3F)ccc2=O)c(F)c1)C(=O)OC1CCCC1] | cyclopentyl N-(2-{4-[6-amino-5-(2,4-difluoro-benzoyl)-2-oxopyridin-1(2H)-yl]-3,5-difluoro-phenyl}ethyl)-L-leucinate | 14 |

CONCLUSIONS

Table 1 demonstrates that the compound of the present inventor is a good inhibitor of p38 MAP kinase. Further, the IC50 values for ester TNF-α inhibition in THP-1 cells and human blood are very low. In particular, the ester TNF-α inhibition in human blood is significantly lower than would be expected given the IC50 values for ester TNF-α inhibition in human blood observed for related compounds.

The AUC data presented in Table 2 show that the bioavailability of the compound of the invention is much higher than that of structurally-similar, known compounds.

The invention claimed is:

1. A compound which is:
  tert-butyl N-[2-{4-[6-amino-5-(2,4-difluorobenzoyl)-2-oxopyridin-1(2H)-yl]-3,5-difluorophenyl}ethyl)-L-alaninate, or a pharmaceutically acceptable salt, hydrate or solvate thereof.

2. A pharmaceutical composition comprising a compound according to claim 1 together with one or more pharmaceutically acceptable carriers and/or excipients.

3. An acid which is:
  N-[2-{4-[6-amino-5-(2,4-difluorobenzoyl)-2-oxopyridin-1(2H)-yl]-3,5-difluorophenyl}ethyl)-L-alanine.

* * * * *